(12) United States Patent  (10) Patent No.: US 7,076,304 B2
Thompson  (45) Date of Patent: Jul. 11, 2006

(54) TRANSCUTANEOUS POWER SUPPLY

(75) Inventor: Marc T. Thompson, Harvard, MA (US)

(73) Assignee: Kidney Replacement Services P.C., Detroit, MI (US)

( * ) Notice: Subject to any disclaimer, the term of this patent is extended or adjusted under 35 U.S.C. 154(b) by 564 days.

(21) Appl. No.: 10/408,329

(22) Filed: Apr. 7, 2003

(65) Prior Publication Data

US 2004/0199213 A1  Oct. 7, 2004

(51) Int. Cl.
*A61N 1/18* (2006.01)
(52) U.S. Cl. .......................... 607/33; 607/60
(58) Field of Classification Search ................... 607/33, 607/29, 34, 55–57, 2
See application file for complete search history.

(56) References Cited

U.S. PATENT DOCUMENTS

| | | |
|---|---|---|
| 5,070,535 A | 12/1991 | Hochmair et al. |
| 5,314,457 A | 5/1994 | Jeutter et al. |
| 5,350,413 A | 9/1994 | Miller |
| 5,702,431 A | 12/1997 | Wang et al. |
| 5,713,939 A | 2/1998 | Nedungadi et al. |
| 6,058,330 A | 5/2000 | Borza |
| 6,240,318 B1 | 5/2001 | Phillips |
| 6,451,055 B1 | 9/2002 | Weiss |
| 6,470,212 B1 | 10/2002 | Weijand et al. |
| 6,475,136 B1 | 11/2002 | Forsell |
| 2002/0177884 A1 | 11/2002 | Ahn et al. |

OTHER PUBLICATIONS

"Development of an Implantable Motor-Driven Assist Pump System,", IEEE Transactions of Biomedical Engrng., vol. 37, No. 2 (Feb. 1990).
George E. Danz, "HIP 4080, 80V High Frequency H-Bridge Driver", Intersill Corp. (1999).

*Primary Examiner*—Robert Pezzuto
*Assistant Examiner*—Joy Patel
(74) *Attorney, Agent, or Firm*—Brooks Kushman P.C.

(57) ABSTRACT

An in-body power supply for supplying energy to an in-body device. The in-body power supply is configured to transfer energy to the in-body device and to compensate for variations and to receive energy without communication between the in-body power supply and an external power source outside the body.

20 Claims, 2 Drawing Sheets

TRANSCUTANEOUS POWER SUPPLY

BACKGROUND OF THE INVENTION

1. Field of the Invention

The present invention relates to in-body power supplies having capabilities to compensate for variations in energy transferred to the in-body power supply without communicating with an out-of-body energy source.

2. Background Art

The present invention relates to transcutaneous power supplies. Transcutaneous power supplies are used to supply energy for driving a device implanted within an animal, usually a human. The power supplies typically include an internal unit for receiving energy from an external unit outside the animal. The internal unit receives the energy and uses it to power an in-body device.

The transmission of energy is dependent on a distance and alignment relationship between the external unit and the internal unit. The transmission variations affect the amount of energy received by the internal unit and the ability to properly supply power to the in-body device. The transmission variations should be compensated to ensure sufficient energy is provided to the in-body device. Some systems have attempted to compensate for the transmission variations by providing a means for internal and external unit to communicate with each other. In general, the communication is used to make adjustments to energy transmission levels between the external and internal units. Such systems are problematic in that they are usually complicated and expensive to design and manufacture.

SUMMARY OF THE INVENTION

The present invention overcomes the above-identified problems with a transcutaneous power supply that compensates for power transmission variations without requiring communication between an in-body power supply and a remote power source.

One aspect of the present invention relates to an in-body power supply for supplying energy to an in-body device. The in-body power supply comprises a receiver for receiving energy from a remote source outside the body. In addition, the in-body power supply comprises a transfer for transferring energy from the receiver to the in-body device. The transfer determines an energy level of the energy and limits energy to be transferred to the in-body device when the energy level exceeds a predetermined threshold. The limiting of the energy allows the in-body energy supply to compensate for variations in the energy received by the receiver without communication between the in-body energy supply and the remote energy source.

Another aspect of the present invention relates to an in-body supply for use in driving to an in-body device. The in-body power supply comprises a transformer for receiving AC magnetic power from a remote source outside the body and generating an AC voltage. In addition, the in-body supply comprises a rectifier for rectifying the AC voltage to a first DC voltage having a voltage level. Still further, the in-body supply comprises a converter for converting the first DC voltage to a second DC voltage when the voltage level of the first DC voltage exceeds a predetermined threshold such that the second DC voltage is for use in driving the in-body device. Yet still further, the in-body power supply comprises a voltage monitor for monitoring the voltage level of the first DC voltage and for bypassing the converter when the level fails to exceed the predetermined threshold such that the first DC voltage is for use in driving the in-body device. The converter and the voltage monitor compensate for variations in alignment between the external and internal units.

Yet another aspect of the present invention relates to a method for transcutaneously providing energy to an in-body device. The method comprises configuring an implantable device to receive energy for a remote energy source outside the body and to transfer energy to the in-body device. The implantable device determines a level of the energy and limits the energy to be transferred to the in-body device when the level exceeds a predetermined threshold. The in-body device can compensate for alignment variations affecting received voltage without communication between the in-body device in the external power source.

DETAILED DESCRIPTION OF THE PREFERRED EMBODIMENT(S)

Figure 1:
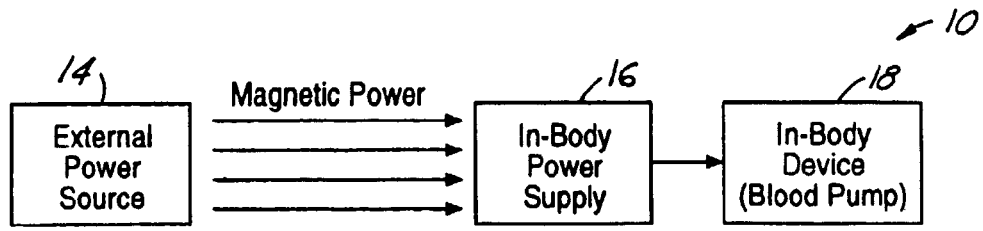
FIG. 1 illustrates a transcutaneous power supply system in accordance with the present invention.

FIG. 1 illustrates a transcutaneous energy supply system 10 accordance with the present invention. The energy supply system 10 includes an external power source 14 and an in-body power supply 16 for use in driving an in-body device 18. The in-body power supply 16 can deliver magnetic power received from the external power source 14 to the in-body device 18. For example, the system can be used to power a blood pump, such as the blood pump disclosed in U.S. Pat. No. 6,439,845 to Veres, entitled Blood Pump and owned by the assignee of the present invention.

The Veres Blood Pump is a centrifugal pump used for renal replacement therapy or as a left ventricular assist pump. The pump is driven by a direct current (DC) electric motor. The in-body power supply 16 can be configured to power the electric motor of the pump with the desired DC power. This and other in-body devices can be powered with the power supply disclosed herewith.

The in-body power supply 16 of the present invention can be implanted within the body of any suitably sized animal. Typically, the power supply 16 is implanted within the body of a human being. As described above in the Background Section, energy supplies are currently implantable within the body of a human being to drive in-body devices, such as, the Veres Blood Pump. These types of energy supplies are commonly referred to as transcutaneous energy supplies.

Simply stated, a transcutaneous power supply is an implantable device for receiving power from an external power source outside the body and using the received energy for driving an in-body blood pump or other device.

The in-body devices 18 powered by the in-body power supply 16 typically require a predetermined level of power for proper operation. In the example referred to above, an electric motor is used to turn the blood pump and pump the blood. Like most motors, the motor turns at a motor speed for pumping the blood. The motor speed is affected by the power supplied from by the in-body power supply. Typically, a higher power results in a faster speed and more pumping of blood and a lower power results in a lower speed and less pumping of blood.

Supplying the motor with a known voltage level is critical for ensuring the blood pump is pumping the desired amount of blood at the desired speed. As it would be undesirable to over drive the motor with too much voltage and pump too much blood and to under drive the motor with too little voltage and pump too little blood, the amount of voltage supplied to the motor should be controllable with the in-body power supply 16.

Figure 2:
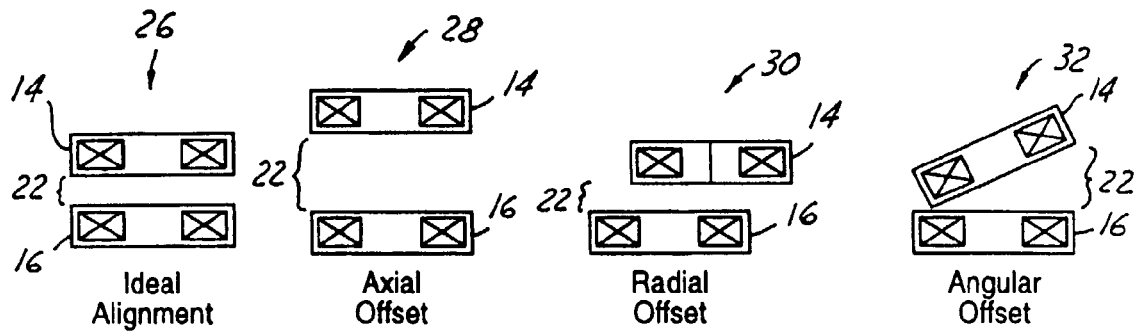
FIG. 2 illustrates a number of diagrams illustrating the affect of various operations on energy transfer from an external power source to an in-body power supply.

To supply the proper amount of power to the in-body device 18, the in-body power supply 16 must compensate for variations in the alignment of the external and internal units. More specifically, the in-body power supply 16 should control at least one of power, current, and voltage supplied to the in-body device 18. FIG. 2 illustrates a number of diagrams illustrating the affect of air gap variations 22 on energy transfer from the external power source 14 to the in-body power supply 16 and the need to control at least one power, current, or voltage to compensate for such variations to ensure the desired voltage is received by the pump.

The air gap 22 between the external power source 14 and the in-body power supply 16 affects the transmission of power received by the in-body power supply 16. An ideal alignment is shown with an ideal alignment diagram 26 and occurs when the external power source 14 and the in-body power supply 16 are aligned at a known axial offset, at a known radial offset, and at a known angular offset. With the ideal alignment, the amount of power received by the in-body power supply 16 is relatively easy to calculate for use in powering the in-body device 18 with the proper amount of power. Some in-body power supplies are designed to operate based on the level of power received at the ideal alignment. Any deviations in power transfer from the ideal alignment requires such in-body power supplies to adjust for non-ideal levels of received power in order to properly power the in-body device, i.e., to operate as if ideal levels of energy were received.

As the in-body power supply 16 and the in-body device 18 are implanted beneath the skin, the location of the in-body power supply 16 is not easily determinable. As such, it is difficult to achieve the ideal alignment. When the external power source 14 is not so precisely aligned with the in-body power supply 16, which commonly occurs, the in-body power supply 16 receives varying amounts of power in accordance to the air gap 22 variations.

The variable air gaps 22 are shown with variations stemming from conditions associated with an axial offset diagram 28, a radial alignment offset diagram 30, and an angular offset diagram 32. In order to compensate for differences in energy transfer associated with these air gap variations 22, some known energy supplies have attempted to provide means for the in-body power supply and external power source to communicate.

Such communication allows the in-body power supply to send a signal to the external energy source for adjusting the amount of power produced by the external energy source, and thereby, affect the amount of power received by the in-body power supply. The signal adjusts the amount of power provided by the external power source until the amount of energy received by the in-body power supply corresponds to a power level sufficient to drive the electric motor of the pump as desired.

The present invention eliminates such communication between the external power source 14 and the in-body power supply 16. Advantageously, the present invention can still compensate for the air gap variations 22 without such communication. The in-body power supply 16 of the present invention provides the in-body device 18 with the proper amount of power to insure the in-body device 18 is pumping the blood at acceptable levels without requiring communication with the external power source 14.

Figure 3:
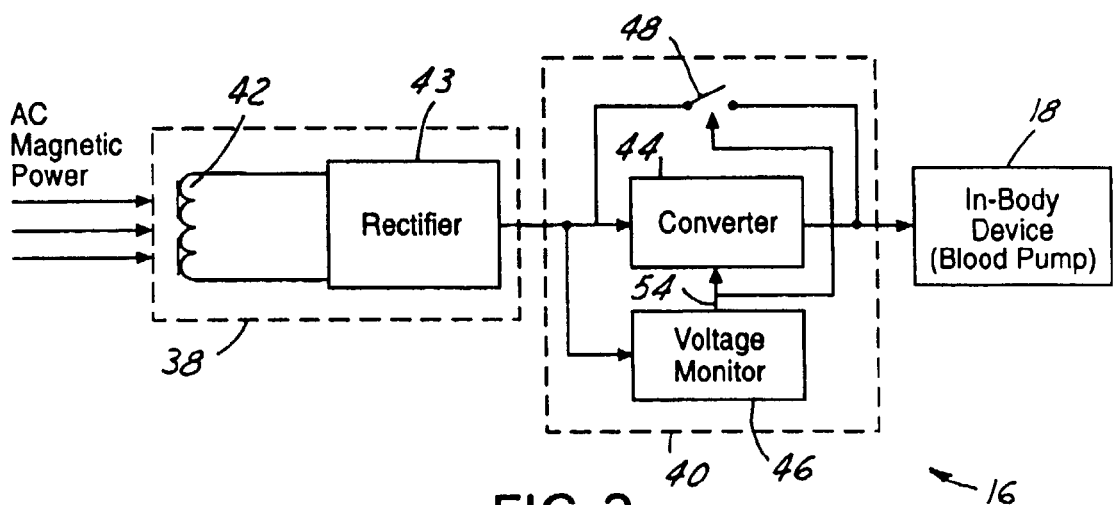
FIG. 3 illustrates an in-body power supply in accordance with the present invention.

Turning to FIG. 3, the ability of the in-body power supply 16 of the present invention to compensate for air gap variations 22 without communication between the in-body power supply 16 and the external power source 14 is now described. The description relates to controlling voltage to ensure the in-body device 18 is driven properly, but it is within the scope and contemplation of the present invention to control power or current. The in-body power supply 16 in accordance with one aspect of the present invention comprises a receiver 38 and a transfer 40. Together, the receiver 38 and the transfer 40 can receive power from a remote source of power located outside of the body, such as the external power source 14, and use the received power for powering the in-body device 18, such as the Veres Blood Pump.

The receiver 38 comprises a secondary side of a transformer 42 and a rectifier 43. The secondary side of the transformer receives AC magnetic power from a primary side of a transformer of the external power source 14 located outside the body. The transformer 42 generates an AC voltage, which is rectified by rectifier 43 to create a first DC voltage.

The transfer 40 transfers power from the receiver 38 to the in-body device 18. The transfer 40 comprises a DC/DC converter 44, a voltage monitor 46, and a bypass 48 to compensate for variations in power from the external power source 14 without communication between the in-body power supply 16 and the external power source 14. Based on the level of received voltage, the transfer 40 can limit the level of the energy to be transferred to the in-body device 18.

The transfer 40 can determine the received voltage levels and limit the amount of power transferred to the in-body device 18, according to the received voltage level, to compensate for air gap variations without communication between the in-body power supply 16 the external power source 14. Rather than requiring the in-body power supply to tell the external power source 14 how much power to provide, the external power source 14 is designed to provide a level of power that is sufficient for the in-body power supply 16 to receive enough power for any of the air gap variations diagrams referred to in FIG. 2.

When the in-body power supply 16 and the external power source 14 are ideally aligned, the amount of voltage received by the in-body power supply is limited before transferring power to the in-body device 18. Typically, such limiting corresponds with a predetermined threshold that is set to a voltage level corresponding with the proper powering of the in-body device 18. When the in-body power supply 16 and the external power source 14 are not so ideally aligned, the amount of voltage received by the in-body power supply 16 may or may not need to be limited according to the severity of the air gap variations.

For example, if the in-body device 18 requires four volts of DC voltage for proper powering, then the transfer 40 limits the power supplied to the in-body device 18 four volts. As such, if the receiver 38 is receiving a level of power producing more than four volts for transfer to the in-body device 18, the transfer 40 limits the voltage to the desired four volts.

The voltage corresponding to the level of energy received is determined by the rectifier 43 rectifying the AC voltage generated by the transformer 42 to a first DC voltage. As such, the first DC voltage corresponds with the voltage associated with the energy received by in-body power supply 16 from the external power source 14. Accordingly, if the first DC voltage is greater than the four volts desired to power the in-body device 18, the transfer 40 must limit the first DC voltage from reaching the in-body device 18. To limit the first DC voltage, the DC/DC converter 44 converts the first DC voltage to a second DC voltage that corresponds with the desired four volts for powering the in-body device 18.

The voltage monitor 46 controls whether the first DC voltage is prevented from reaching the in-body device by determining whether the first DC voltage is greater than the second DC voltage. The voltage monitor 46 comprises an integrated circuit for comparing the first DC voltage to the desired second DC voltage. A signal 54 is generated in response to whether the first DC voltage is greater than the second DC voltage. If the first DC voltage is greater than the second DC voltage, then the signal 54 can control the converter 44 to limit the first DC voltage to the second DC voltage and to transfer the second DC voltage to the in-body device 18. If the first DC voltage is less than the second DC voltage, then the signal 54 can control the bypass 48 for bypassing the converter 44 and to transfer the first DC voltage directly to the in-body device.

The voltage monitor 46 compensates for energy transfer variations stemming from the air gap variations shown in FIG. 2 by either allowing the first DC voltage to bypass the converter 44 or by allowing the first DC voltage to be converted by the converter 44 to the second DC voltage. The voltage monitor 46 turns off the bypass 48 and turns on the converter 44 to limit the first DC voltage to power the in-body device 18 with the second DC voltage, and the voltage monitor 46 turns on the bypass 48 and turns off the converter 44 to bypass the converter to power the in-body device 18 with the first DC voltage pump. The in-body device 18 is powered by one of the first DC voltage or by the second DC voltage.

Figure 4:
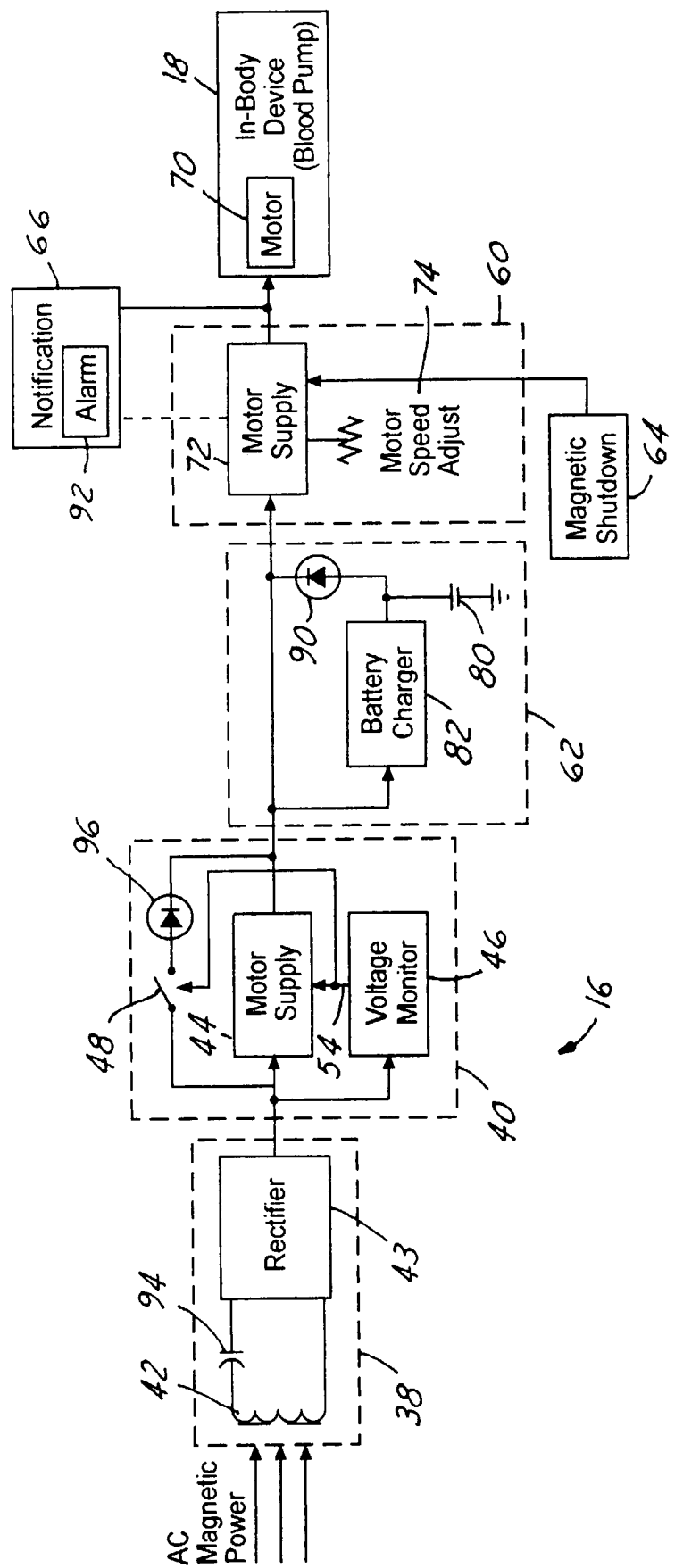
FIG. 4 illustrates the in-body power supply including additional features and in accordance with the present invention.

FIG. 4 illustrates additional features of the present invention, such as a motor driving circuit 60, a battery power supply circuit 62, a magnetic shutdown 64, and a notification 66. These and other features can be included with the in-body power supply 16 of the present invention to facilitate the implementation of the present invention with different in-body devices 18. The features shown in FIG. 4 are particularly advantageous for use with in-body devices like the Veres Blood Pump.

The motor driver 60 receives power from the transfer 40 for driving a motor 70 of the in-body blood pump. The motor driver 60 includes a motor supply 72 and a motor speed adjust 74 for fine tuning the voltage provided to the motor 70 to achieve the desired pumping speed.

The motor supply 72 is similar to the converter in that the motor supply 72 limits the received voltage and provides a corresponding constant voltage to the motor 70 for driving the motor 70 at the desired pumping speed. Typically, the motor supply 72 can operate the pump properly at power levels lower than the power levels associated with the second DC voltage, but at some level the power received from the transfer circuit is too low and the motor driving 72 cannot provide sufficient power the motor 70 for turning the pump at the desired speed.

The motor speed adjust 74, as shown, is adjusted before implanting the in-body power supply within the body. Accordingly, the in-body power supply can be a standard product that can be easily adjusted to provide varying levels of voltage for driving a number of motors. This is particularly advantageous as it may be desired to power pumps at different speeds depending on the particular needs of the animal having the pump or other implantable devices.

The magnetic shut down 64 can be used to shut down the motor driver 72 from outside the body to prevent the in-body device 18 from pumping blood. The magnetic shutdown 64 can receive a magnetic signal from a permanent magnet to shut down the motor supply 72.

The battery supply 62 supplies power to the motor supply 72 for use in powering the motor 70 when the power level transferred to the motor driver 72 is too low to allow the motor driver 72 to properly supply the pump.

The battery supply 62 can be used to supply power to the motor supply 72 when the transfer 40 is transferring power to the motor supply 72 and when the transfer 40 is not transferring power to the motor supply 72. The battery power supply 62 determines when to supply power to the motor supply 72 without communicating with the external power source 14.

The battery supply 62 can detect the level of voltage supplied by the transfer 40 and determine whether additional power is need to properly supply the motor supply 72. If the power transferred from the transfer 40 is insufficient to properly power the motor supply 72, the battery supply circuit 62 is used to supply additional power to the motor supply 72. The battery supply circuit 62 can determine how much additional power is need by the motor supply 72 and supply the corresponding amount of power.

The battery supply 62 comprises a rechargeable battery 80 and a battery charger 82. The battery 80 supplies power to the motor supply 72. The battery charger 82 and diode 90 instruct the battery 80 to supply power when the power transferred to the motor supply 72 is insufficient for properly powering the motor driving circuit.

The second DC voltage can be selected to allow the second DC voltage to power both the motor supply 72 and recharge the battery 80. The battery charger 82 detects whether the power transferred by the transfer 40 includes sufficient voltage for recharging the battery 80. Typically, the second DC voltage is sufficient for both powering the motor supply 72 and recharging the battery 80.

The air gap variations can affect the amount of voltage received by the receiver 38 and make it impossible for the transfer 40 to transfer the second DC voltage. When the second DC voltage is not transferred, the converter is bypassed and the received voltage, i.e., the first DC voltage, is transferred to the motor driver 72 without any limiting by the converter 44. The first DC voltage may or may not be sufficient for both powering the motor driving circuit and recharging the battery.

The motor driver 72 can be configured to properly power the motor 70 at voltage levels higher or lower than the second DC voltage. As such, the motor driver 72 can still operate properly in some cases when the first DC voltage is transferred to the motor driver 72. The battery charger 82 detects whether the first DC voltage is sufficient for both powering the motor driver 72 and recharging the battery 80. If the first DC voltage is insufficient for both powering the motor driving circuit and recharging the battery, the battery charger 82 prevents recharging of the battery 80.

If the first DC voltage or the second DC voltage is sufficient for both powering the motor driving circuit and recharging the battery, the battery charger 82 allows power to flow to the battery 80 for recharging the battery. The battery charger 62 includes an integrated circuit, like the voltage monitoring circuit, for determining whether to recharge the battery 80.

The battery charging 82 can be configured to communicate with the motor driving circuit 60 for use in charging the battery 80. More specifically, the motor driving circuit 60 can shut down the motor driver 72 using the magnetic shutdown 64 and communicate the shut down to the battery charger 82 for allowing the battery charger 82 to permit recharging of the battery 80 under all levels of power transferred by the transfer 40.

The notifier 66 is used to determine whether sufficient power is being supplied to the in-body device 18. An alarm 92 is generated when insufficient power is provided to the in-body device 18. This feature can be advantageous for determining when charging of the battery 80 is needed.

A number of other features, such as, a tank capacitor 94 and a second diode 96 can also be included with the in-body power supply 16. The diodes 90 and 96 prevent the current from back flowing when the receiver 38 is not receiving power. The tank capacitor 94 limits noise and fine tunes the current when the receiver 38 is receiving power. Additional features could also be included depending on the particular in-body device and are within the contemplation of the present invention.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An in-body power supply for supplying energy to drive an in-body device, the in-body power supply comprising:
    a receiver for receiving energy from an external power source outside the body; and
    a transfer for transferring energy from the receiver to the in-body device, wherein the transfer determines an energy level of the energy and limits the energy to be transferred to the in-body device when the energy level exceeds a predetermined threshold such that variations in energy from the external power source are compensated for without communication between the in-body power supply and the external power source.

2. The in-body power supply of claim 1 wherein the transfer controls voltage and comprises a converter for limiting a voltage level corresponding with the energy level when the energy level exceeds the predetermined threshold, and a bypass for bypassing the converter when the energy level fails to exceed the predetermined threshold.

3. The in-body power supply of claim 2 wherein the transfer comprises a voltage monitor for determining the voltage level.

4. The in-body power supply of claim 1 further comprising a battery supply for supplying energy to the in-body device, wherein the battery supply determines when to supply energy to the in-body device without communicating with the external power source.

5. The in-body power supply of claim 4 wherein the battery supply comprises a rechargeable battery for supplying energy to the in-body device, wherein the battery supply further determines whether the energy transferred to the in-body device by the transfer is sufficient for simultaneously charging the battery and supplying sufficient energy to the in-body device.

6. The in-body power supply of claim 1 wherein the in-body device is a motor and the in-body power supply includes a motor driver for receiving the energy from the transfer for use in driving the motor.

7. The in-body power supply of claim 6 further comprising a magnetic shutdown for receiving a magnetic signal from a permanent magnet for use in shutting down the motor driver.

8. The in-body power supply of claim 7 further comprising a motor speed adjust for use in adjusting motor speed.

9. The in-body power supply of claim 1 further comprising a notifier for determining whether sufficient energy is being supplied to the in-body device and generating an alarm when insufficient energy is supplied to the in-body device.

10. An in-body supply for use in driving an in-body device, the in-body supply comprising:
    a transformer for receiving AC magnetic power from an external power source outside the body and generating an AC voltage;
    a rectifier for rectifying the AC voltage to a first DC voltage having a voltage level;
    a converter for converting the first DC voltage to a second DC voltage when the voltage level of the first DC voltage exceeds a predetermined threshold such that the second DC voltage is for use in driving the in-body device; and
    a voltage monitor for monitoring the voltage level of the first DC voltage and for bypassing the converter when the voltage level fails to exceed the predetermined threshold such that the first DC voltage is for use in driving the in-body device, wherein the converter and voltage monitor compensate for alignment variations affecting voltage without communication between the in-body device and the external power source.

11. The apparatus of claim 10 wherein the voltage monitor comprises an integrated circuit for use in activating a bypass switch for bypassing the converter.

12. The apparatus of claim 10 further comprising a battery supply for supplying voltage to the in-body device if the voltage from either the first DC rectified voltage or the second DC converted voltage is insufficient to power the in-body device.

13. The apparatus of claim 12 wherein the battery supply includes an integrated battery circuit for determining whether the voltage from either the first DC rectified voltage or the second DC converted voltage is insufficient to power the in-body device.

14. The apparatus of claim 13 wherein the battery supply comprises a rechargeable battery for supplying voltage to the in-body device and being rechargeable with the voltage from either the first DC rectified voltage or the second DC converted voltage, wherein the integrated battery circuit determines whether the voltage from either the first DC rectified voltage or the second DC converted voltage is sufficient for charging the battery and sufficiently powering the in-body device.

15. A method for transcutaneously providing energy to an in-body device, the method comprising:
    configuring an implantable device to receive energy from an external power source outside the body and to transfer energy to the in-body device, wherein the implantable device determines an energy level of the energy and limits the energy to be transferred to the in-body device when the energy level exceeds a predetermined threshold such that variations in alignment affecting voltage received from the external power source are compensated for without communication between the in-body power supply and the external power source.

16. The method of claim 15 further comprising implanting the implantable device within a body of an animal.

17. The method of claim 15 wherein the implantable device controls voltage and comprises a converter for limiting a voltage level corresponding with the energy level when the energy level exceeds the predetermined threshold, and a bypass for bypassing the converter when the energy level of the energy fails to exceed the predetermined threshold.

18. The method of claim 17 wherein the implantable device comprises a voltage monitor for determining the level of the voltage.

19. The method of claim 15 wherein the implantable device comprises a battery supply for supplying energy to the in-body device, wherein the battery supply determines when to supply energy to the in-body device without communicating with the external power source.

20. The in-body power supply of claim 19 wherein the battery supply further comprises a rechargeable battery for supplying energy to the in-body device, and the energy supply circuit is configured to determine whether the energy being transferred to the in-body device is sufficient for simultaneously charging the battery and supplying sufficient power to the in-body device.

* * * * *